(12) United States Patent
DelVecchio

(10) Patent No.: US 6,228,576 B1
(45) Date of Patent: May 8, 2001

(54) HEPATITIS C VIRUS NS5B TRUNCATED PROTEIN AND METHODS THEREOF TO IDENTIFY ANTIVIRAL COMPOUNDS

(75) Inventor: Alfred M. DelVecchio, West Chester, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/208,140

(22) Filed: Dec. 9, 1998

Related U.S. Application Data

(60) Provisional application No. 60/069,208, filed on Dec. 11, 1997.

(51) Int. Cl.[7] ....................................... C12Q 1/70
(52) U.S. Cl. ............................ 435/5; 435/7.4; 530/350
(58) Field of Search .......................... 530/350; 436/501, 436/517, 2; 435/5, 6, 7.4, 7.6, 7.93

(56) References Cited

U.S. PATENT DOCUMENTS 5,861,267   1/1999   Su ........................................ 435/23

FOREIGN PATENT DOCUMENTS

| 0 318 216 B1 | 5/1989 | (EP) . |
| 644 894 | 5/1997 | (EP) . |
| WO 96/36619 | 11/1996 | (WO) . |
| WO 96/37619 | 11/1996 | (WO) . |
| WO 97/12033 | 4/1997 | (WO) . |
| WO 97/47358 | 12/1997 | (WO) . |

OTHER PUBLICATIONS

USPTO Sequence Search of SEQ ID No.:4 using GenCore version 4.5, Jan. 2000.*

Kolykhalov, A.A. et al., "Transmission of Hepatitis C by Intrahepatic Inoculation with Transcribed RNA", *Science*, 277, pp. 570–574 (1997).

Yanagi, M. et al., "Transcripts From a Single Full–Length cDNA Clone of Hepatitis C Virus are Infectious when Directly Transfected into the Liver of a Chimpanzee", *PNAS USA*, 94, pp. 8738–8743 (1997).

Inchauspe, G. et al., "Genomic Structure of the Human Proptotype Strain H of Hepatitis C Virus: Comparison with American and Japanese Isolates", *PNAS USA*, 88, pp. 10292–10296 (1991).

Ferrari, E. et al., "Characterization of Soluble Hepatitis C Virus RNA–Dependent RNS Polymerase Expressed in Escherichia", *Hepatology*, 28(4), Abstract #632 (1998).

Lohman, et al., "Biochemical Properties of Hepatitis C Virus NS5B RNA–Dependent RNA Polymerase and Identification of Amino Acid Sequence Motifs Essential for Enzymatic Activity", *Journal of Virology* 71(11): 8416–8428 (1997).

Yamashita, et al., "RNA–Dependent RNA Polymerase Activity of the Soluble Recominant Hepatitis C Virus NS5B Protein Truncated at the C–terminal Region", *Journal of Biological Chemistry* 273(25): 15479–15486 (1998).

* cited by examiner

*Primary Examiner*—Donna C. Wortman
*Assistant Examiner*—Robert A. Zeman
(74) *Attorney, Agent, or Firm*—William T. Han; William T. King; Charles M. Kinzig

(57) ABSTRACT

The invention provides HCV NS5B polypeptides and DNA (RNA) encoding HCV NS5B polypeptides and methods for producing such polypeptides by recombinant techniques. Also provided are methods for utilizing HCV NS5B polypeptides to screen for antiviral compounds.

2 Claims, No Drawings

HEPATITIS C VIRUS NS5B TRUNCATED PROTEIN AND METHODS THEREOF TO IDENTIFY ANTIVIRAL COMPOUNDS

CROSS-REFERENCE TO RELATED APPLICATION

This application claims benefit to the earlier provisional U.S. application, Ser. No. 60/069,208, filed on Dec. 11, 1997, the contents of which are incorporated herein by reference in their entirety.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of viruses of the Flaviviridae family, particularly a novel truncate of the Hepatitis C Virus (HCV) NS5B protein, as well as other variants disclosed herein, all hereinafter referred to as "HCV NS5B".

BACKGROUND OF THE INVENTION

First identified by molecular cloning in 1989 (Choo, et al., *Science* 244: 359–362 (1989)), hepatitis C virus (HCV) is now widely accepted as the most common causative agent of post-transfusion non A, non-B hepatitis (NANBH) (Kuo, et al., *Science* 244:362–364 (1989)). Infection with HCV is a major cause of human liver disease throughout the world with seroprevalence in the general population ranging from 0.3 to 2.2% (van der Poel, et al., HEPATITIS C VIRUS; Amsterdam: Karger; pp. 137–163 (1994)) to as high as ~10–20% in Egypt (Hibbs, et al., *J. Infect. Dis.* 168: 789–790 (1993)). Although the virus is most commonly transmitted via blood, the mode of transmission remains unknown for a large portion of infected individuals (Alter, M. J., *Infect. Agents Dis.* 2: 155–166 (1993)). Over 50% of infections by HCV progress to acute hepatitis associated with viremia and generally elevated serum alanine aminotranferase (ALT) levels (Alter, H. J., CURRENT PROSPECTIVES IN HEPATOLOGY; New York: Plenum; pp. 83–97 (1989)). Over half of the acute cases progress to a chronic infection with roughly 20% developing cirrhosis (Alter, H. J., supra). Chronic infection by HCV has also been linked epidemiologically to the development of hepatocellular carcinoma (HCC), especially in cirrhotic patients (Blum, et al., *Hepatology* 19: 251–258 (1994)).

Since its initial identification, many isolates of HCV have been sequenced, displaying much genetic diversity and leading to the subclassification of this virus into multiple genotypes. See, e.g., Bukh, et al., *Proc. Natl. Acad. Sci. USA* 90:8234–8238 (1993); Bukh, et al., *Proc. Natl. Acad. Sci. USA* 91: 8239–8243 (1994); Dusheiko, et al., *Hepatology* 19: 13–18 (1994)). Due to its genome structure and sequence homology, this virus was assigned as a new genus in the Flaviviridae family, along with the other two genera, flaviviruses (such as yellow fever virus and Dengue virus types 1–4) and pestiviruses (such as bovine viral diarrhea virus). See, e.g., Choo, et al., supra; Miller, et al., *Proc. Natl. Acad. Sci. USA* 87: 2057–2061 (1990)). Like the other members of the Flaviviridae family, HCV is an enveloped virus containing a single-stranded RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang, et al., *Curr. Topics Microbiol. Immunol.* 203: 99–112 (1995)). This element is followed by a region which encodes a single long open reading frame (ORF) encoding a polypeptide of ~3000 amino acids comprising both the structural and nonstructural viral proteins. This large polypeptide is subsequently processed into the individual structural and nonstructural proteins by a combination of host and virally-encoded proteinases (reviewed in Rice, VIROLOGY; Raven Press: New York, 2nd Ed.; pp. 931–960 (1996)). In their respective order in the polyprotein precursor from amino-terminus to carboxy-terminus, are core-E1-E2-p7-NS2-NS3-NS4A-NS4B-NS5A-NS5B.

Inhibition of the biological activity of viral proteins of the Flaviviridae family, particularly HCV NS5B, is potentially of benefit in controlling, reducing and alleviating the diseases caused by infection with these viral organisms. Clearly, there is a need for factors, such as the novel compounds of the invention, that have a present benefit of being useful to screen compounds for antiviral activity. Such factors are also useful in determining their role in pathogenesis of infection, dysfunction and disease. There is also a need for identification and characterization of such factors and their antagonists and agonists which can play a role in preventing, ameliorating or correcting infections, dysfunctions or diseases.

In an attempt to identify the critical domains of the HCV NS5B protein, Lohmann, et al., *J. Virol.* 8416–8428 (1997) truncated both the amino and carboxy termini of the full-length HCV NS5B protein. While Lohmann, et al. discuss various sequence fragments of the HCV NS5B protein, with one exception of a known GenBank sequence, the reference does not specifically disclose either the cDNA or amino acid sequences of the these fragments.

Clearly, there is a need to discover new antiviral compounds that are useful in the cure, treatment, and prevention of virus infection of the Flaviviridae family, particularly HCV. Because the HCV NS5B protein is difficult to express, it is important to discover forms of the protein which may be more soluble for use in a drug-discovery screen than is the full-length HCV NS5B protein. The instant invention is believed to provide for such a need in the antiviral area.

SUMMARY OF THE INVENTION

It is an object of the invention to provide polypeptides that have been identified as novel HCV NS5B polypeptides by homology between the amino acid sequence set forth in Table 2 [SEQ ID NO:2] and other known HCV amino acid sequences, such as those shown in Table 4.

It is a further object of the invention to provide polynucleotides that encode these novel HCV NS5B polypeptides, particularly polynucleotides that encode the polypeptide, herein designated HCV NS5B.

In a particularly preferred embodiment of the invention, there is provided a polynucleotide which comprises a region encoding the HCV NS5B polypeptides set forth in Table 3 [SEQ ID NO:3] and which includes, for example, one or more variants thereof.

In another particularly preferred embodiment of the invention, there is a novel truncation mutant of the HCV NS5B protein comprising the amino acid sequence set forth in Table 3 [SEQ ID NO:4], or one or more variants thereof.

In a further aspect of the invention there are provided isolated nucleic acid molecules encoding HCV NS5B, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of HCV NS5B polypeptides.

Another aspect of the invention provides novel polypeptides of HCV NS5B, as well as biologically, diagnostically, prophylactically, clinically or therapeutically useful variants thereof, and compositions comprising the same.

Among the particularly preferred embodiments of the invention are variants of HCV NS5B polypeptide encoded by naturally occurring alleles of the HCV NS5B gene.

In a preferred embodiment of the invention, there are provided methods for producing the aforementioned HCV NS5B polypeptides.

In accordance with yet another aspect of the invention, there are provided for inhibitors to such polypeptides, useful as antiviral agents, including, for example, antibodies.

In accordance with certain preferred embodiments of the invention, there are provided products, compositions and methods for assessing HCV NS5B expression, treating disease, for example, viruses linked to the family, particularly HCV; flaviviruses such as yellow fever virus; Dengue virus types 1–4; and pestiviruses, such as bovine viral diarrhea virus and classic swine fever, among others, assaying genetic variation, and administering a HCV NS5B polypeptide or polynucleotide to an organism to raise an immunological response against a virus of the Flaviviridae family, especially HCV NS5B.

In accordance with certain preferred embodiments of this and other aspects of the invention there are provided polynucleotides that hybridize to HCV NS5B polynucleotide sequences, particularly under stringent conditions.

In certain preferred embodiments of the invention there are provided antibodies against HCV NS5B polypeptides.

In other embodiments of the invention, there are provided methods for identifying compounds which bind to or otherwise interact with and inhibit, or activate, an activity of a polypeptide or polynucleotide of the invention comprising: contacting a polypeptide or polynucleotide of the invention with a compound to be screened under conditions to permit binding to, or other interaction between, the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided HCV NS5B agonists and antagonists, preferably virustatic agonists and antagonists.

In a further aspect of the invention there are provided compositions comprising an HCV NS5B polynucleotide or polypeptide for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed, transfected or infected, or is capable of transformation, transfection of infection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., *SIAM J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, et al., *Nucleic Acids Research* 12(1): 387 (1984)), BLASTP, BLASTN, and FASTA (Atschul, et al., *J. Molec. Biol.* 215: 403–410 (1990). The BLAST X program is publicly available from NCBI and other sources (BLAST Manual, Altschul, S., et al., NCBI NLM NIH Bethesda, Md. 20894; Altschul, et al., *J. Mol. Biol.* 215: 403–410 (1990).

As an illustration, by a polynucleotide having a nucleotide sequence having at least, for example, 95% "identity" to a reference nucleotide sequence of SEQ ID NO:3, it is intended that the nucleotide sequence of the polynucleotide is identical to the reference sequence, except that the polynucleotide sequence may include up to five point mutations per each 100 nucleotides of the reference nucleotide sequence of SEQ ID NO:3. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:4, it is intended that the amino acid sequence of the polypeptide is identical to the reference sequence except that the polypeptide sequence may include up to five amino acid alterations per each 100 amino acids of the reference amino acid of SEQ ID NO:4. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)", as it is employed herein, embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter, et al., *Meth. Enzymol.* 182:626–646 (1990) and Rattan, et al., Protein Synthesis: Posttranslational Modifications and Aging, *Ann. N.Y. Acad. Sci.* 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DETAILED DESCRIPTION OF THE INVENTION

The full-length HCV NS5B nucleotide and amino acid sequences are set forth in Table 2 [SEQ ID NO:1 and SEQ ID NO:2, respectively].

TABLE 2

Polynucleotide Sequence of HCV NS5B [SEQ ID NO:1]
TC AATGTCTTAT

| | | | | | |
|---|---|---|---|---|---|
| 11801 | ACCTGGACAG | GCGCACTCGT | CACCCCGTGC | GCTGCGGAAG | AACAAAAACT |
| 11851 | GCCCATCAAC | GCACTGAGCA | ACTCGTTGCT | ACGCCATCAC | AATCTGGTAT |
| 11901 | ATTCCACCAC | TTCACGCAGT | GCTTGCCAAA | GGCAGAAGAA | AGTCACATTT |
| 11951 | GACAGACTGC | AAGTTCTGGA | CAGCCATTAC | CAGGACGTGC | TCAAGGAGGT |
| 12001 | CAAAGCAGCG | GCGTCAAAAG | TGAAGGCTAA | CTTGCTATCC | GTAGAGGAAG |
| 12051 | CTTGCAGCCT | GACGCCCCCA | CATTCAGCCA | AATCCAAGTT | TGGCTATGGG |
| 12101 | GCAAAAGACG | TCCGTTGCCA | TGCCAGAAAG | GCCGTAGCCC | ACATCAACTC |
| 12151 | CGTGTGGAAA | GACCTTCTGG | AAGACAGTGT | AACACCAATA | GACACTATCA |
| 12201 | TCATGGCCAA | GAACGAGGTC | TTCTGCGTTC | AGCCTGAGAA | GGGGGGTCGT |
| 12251 | AAGCCAGCTC | GTCTCATCGT | GTTCCCCGAC | CTGGGCGTGC | GCGTGTGCGA |
| 12301 | GAAGATGGCC | CTGTACGACG | TGGTTAGCAA | ACTCCCCCTG | GCCGTGATGG |
| 12351 | GAAGCTCCTA | CGGATTCCAA | TACTCACCAG | GACAGCGGGT | TGAATTCCTC |
| 12401 | GTGCAAGCGT | GGAAGTCCAA | GAAGACCCCG | ATGGGGTTCC | CGTATGATAC |
| 12451 | CCGCTGTTTT | GACTCCACAG | TCACTGAGAG | CGACATCCGT | ACGGAGGAGG |
| 12501 | CAATTTACCA | ATGTTGTGAC | CTGGACCCCC | AAGCCCGCGT | GGCCATCAAG |
| 12551 | TCCCTCACTG | AGAGGCTTTA | TGTTGGGGGC | CCTCTTACCA | ATTCAAGGGG |
| 12601 | GGAAAACTGC | GGCTATCGCA | GGTGCCGCGC | GAGCGGCGTA | CTGACAACTA |
| 12651 | GCTGTGGTAA | CACCCTCACT | TGCTACATCA | AGGCCCGGGC | AGCCCGTCGA |
| 12701 | GCCGCAGGGC | TCCAGGACTG | CACCATGCTC | GTGTGTGGCG | ACGACTTAGT |
| 12751 | CGTTATCTGT | GAAAGTGCGG | GGGTCCAGGA | GGACGCGGCG | AGCCTGAGAG |
| 12801 | CCTTTACGGA | GGCTATGACC | AGGTACTCCG | CCCCCCCCGG | GGACCCCCCA |
| 12851 | CAACCAGAAT | ACGACTTGGA | GCTTATAACA | TCATGCTCCT | CCAACGTGTC |
| 12901 | AGTCGCCCAC | GACGGCGCTG | GAAAAAGGGT | CTACTACCTT | ACCCGTGACC |
| 12951 | CTACAACCCC | CCTCGCGAGA | GCCGCGTGGG | AGACAGCAAG | ACACACTCCA |
| 13001 | GTCAATTCCT | GGCTAGGCAA | CATAATCATG | TTTGCCCCCA | CACTGTGGGC |
| 13051 | GAGGATGATA | CTGATGACCC | ATTTCTTTAG | CGTCCTCATA | GCCAGGGATC |
| 13101 | AGCTTGAACA | GGCTCTTAAC | TGTGAGATCT | ACGCAGCCTG | CTACTCCATA |
| 13151 | GAACCACTGG | ATCTACCTCC | AATCATTCAA | AGACTCCATG | GCCTCAGCGC |
| 13201 | ATTTTTACTC | CACAGTTACT | CTCCAGGTGA | AGTCAATAGG | GTGGCCGCAT |
| 13251 | GCCTCAGAAA | ACTTGGGGTC | CCGCCCTTGC | GAGCTTGGAG | ACACCGGGCC |
| 13301 | CGGAGCGTCC | GCGCTAGGCT | TCTGTCCAGG | GGAGGCAGGG | CTGCCATATG |
| 13351 | TGGCAAGTAC | CTCTTCAACT | GGGCAGTAAG | AACAAAGCTC | AAACTCACTC |
| 13401 | CAATAGCGGC | CGCTGGCCGG | CTGGACTTGT | CCGGTTGGTT | CACGGCTGGC |
| 13451 | TACAGCGGGG | GAGACATTTA | TCACAGCGTG | TCTCATGCCC | GGCCCCGC |

Polypeptide Sequence of HCV NS5B [SEQ ID NO:2]

| | | | | | |
|---|---|---|---|---|---|
| 1 | SMSYTWTGAL | VTPCAAEEQK | LPINALSNSL | LRHHNLVYST | TSRSACQRQK |
| 51 | KVTFDRLQVL | DSHYQDVLKE | VKAAASKVKA | NLLSVEEACS | LTPPHSAKSK |
| 101 | FGYGAKDVRC | HARKAVAHIN | SVWKDLLEDS | VTPIDTTIMA | KNEVFCVQPE |

TABLE 2-continued

| | | | | |
|---|---|---|---|---|
| 151 | KGGRKPARLI | VFPDLGVRVC | EKMALYDVVS | KLPLAVMGSS | YGFQYSPGQR |
| 201 | VEFLVQAWKS | KKTPMGFSYD | TRCFDSTVTE | SDIRTEEAIY | QCCDLDPQAR |
| 251 | VAIKSLTERL | YVGGPLTNSR | GENCGYRRCR | ASGVLTTSCG | NTLTCYIKAR |
| 301 | AACRAAGLQD | CTMLVCGDDL | VVICESAGVQ | EDAASLRAFT | EAMTRYSAPP |
| 351 | GDPPQPEYDL | ELITSCSSNV | SVAHDGAGKR | VYYLTRDPTT | PLARAAWETA |
| 401 | RHTPVNSWLG | NIIMFAPTLW | ARMILMTHFF | SVLIARDQLE | QALNCEIYGA |
| 451 | CYSIEPLDLP | PIIQRLHGLS | AFSLHSYSPG | EINRVAACLR | KLGVPPLRAW |
| 501 | RHRARSVRAR | LLSRGGRAAI | CGKYLFNWAV | RTKLKLTPIP | AAGRLDLSGW |
| 551 | FTAGYSGGDI | YHSVSHARPR | WFWFCLLLLA | AGVGIYLLPN | R |

A particularly preferred embodiment of the invention relates to the HCV NS5B truncation mutant having the nucleotide and amino acid sequences set out in Table 3 [SEQ ID NO:3 and SEQ ID NO:4, respectively].

TABLE 3

HCV NS5B Truncation Mutant Polynucleotide Sequence [SEQ ID NO:3]

| | | | | |
|---|---|---|---|---|
| 1 | TCAATGTCTT | ATTCCTGGAC | AGGCGCACTC | GTCACCCCGT | GCGCTGCGGA |
| 51 | AGAACAAAAA | CTGCCCATCA | ACGCACTGAG | CAACTCGTTG | CTACGCCATC |
| 101 | ACAATCTGGT | GTATTCCACC | ACTTCACGCA | GTGCTTGCCA | AAGGCAGAAG |
| 151 | AAAGTCACAT | TTGACAGACT | GCAAGTTCTG | GACAGCCATT | ACCAGGACGT |
| 201 | GCTCAAGGAG | GTCAAAGCAG | CGGCGTCAAA | AGTGAAGGCT | AACTTGCTAT |
| 251 | CCGTAGAGGA | AGCTTGCAGC | CTGACGCCCC | ACATTCAGC | CAAATCCAAG |
| 301 | TTTGGCTATG | GGGCAAAAGA | CGTCCGTTGC | CATGCCAGAA | AGGCCGTAGC |
| 351 | CCACATCAAC | TCCGTGTGGA | AGACCTTCT | GGAAGACAGT | GTAACACCAA |
| 401 | TAGACACTAC | CATCATGGCC | AAGAACGAGG | TTTTCTGCGT | TCAGCCTGAG |
| 451 | AAGGGGGGTC | GTAAGCCAGC | TCGTCTCATC | GTGTTCCCCG | ACCTGGGCGT |
| 501 | GCGCGTGTGC | GAGAAGATGG | CCCTGTACGA | CGTGGTTAGC | AAGCTCCCCC |
| 551 | TGGCCGTGAT | GGGAAGCTCC | TACGGATTCC | AATACTCACC | AGGACAGCGG |
| 601 | GTTGAATTCC | TCGTGCAAGC | GTGGAAGTCC | AAGAAGACCC | CGATGGGGTT |
| 651 | CTCGTATGAT | ACCCGCTGTT | TTGACTCCAC | AGTCACTGAG | AGCGACATCC |
| 701 | GTACGGAGGA | GGCAATTTAC | CAATGTTGTG | ACCTGGACCC | CCAAGCCCGC |
| 751 | GTGGCCATCA | AGTCCCTCAC | TGAGAGGCTT | TATGTTGGGG | GCCCTCTTAC |
| 801 | CAATTCAAGG | GGGGAAAACT | GCGGCTACCG | CAGGTGCCGC | GCGAGCGGCG |
| 851 | TACTGACAAC | TAGCTGTGGT | AACACCCTCA | CTTGCTACAT | CAAGGCCCGG |
| 901 | GCAGCCTGTC | GAGCCGCAGG | GCTCCAGGAC | TGCACCATGC | TCGTGTGTGG |
| 951 | CGACGACTTA | GTCGTTATCT | GTGAAAGTGC | GGGGGTCCAG | GAGGACGCGG |
| 1001 | CGAGCCTGAG | AGCCTTCACG | GAGGCTATGA | CCAGGTACTC | CGCCCCCCCC |
| 1051 | GGGGACCCCC | CACAACCAGA | ATACGACTTG | GAGCTTATAA | CATCATGCTC |
| 1101 | CTCCAACGTG | TCAGTCGCCC | ACGACGGCGC | TGGAAAGAGG | GTCTACTACC |
| 1151 | TTACCCGTGA | CCCTACAACC | CCCCTCGCGA | GAGCCGCGTG | GGAGACAGCA |
| 1201 | AGACACACTC | CAGTCAATTC | CTGGCTAGGC | AACATAATCA | TGTTTGCCCC |

TABLE 3-continued

```
1251 CACACTGTGG GCGAGGATGA TACTGATGAC CCATTTCTTT AGCGTCCTCA

1301 TAGCCAGGGA TCAGCTTGAA CAGGCTCTTA ACTGTGAGAT CTACGGAGCC

1351 TGCTACTCCA TAGAACCACT GGATCTACCT CCAATCATTC AAAGACTCCA

1401 TGGCCTCAGC GCATTTTCAC TCCACAGTTA CTCTCCAGGT GAAATCAATA

1451 GGGTGGCCGC ATGCCTCAGA AAACTTGGGG TCCCGCCCTT GCGAGCTTGG

1501 AGACACCGGG CCCGGAGCGT CCGCGCTAGG CTTCTGTCCA GAGGAGGCAG

1551 GGCTGCCATA TGTGGCAAGT ACCTCTTCAA CTGGGCAGTA AGAACAAAGC

1601 TCAAACTCAC TCCAATAGCG GCCGCTGGCC GGCTGGACTT GTCCGGTTGG

1651 TTCACGGCTG GCTACAGCGG GGGAGACATT TATCACAGCG TGTCTCATGC

1701 CCGGCCCCGC
```

| HCV NS5B Truncation Mutant Polypeptide<br>Sequence [SEQ ID NO:4] | | | | |
|---|---|---|---|---|
| 1 | SMSYSWTGAL | VTPCAAEEQK | LPINALSNSL | LRHHNLVYST | TSRSACQRQK |
| 51 | LRHHNLVYST | TSRSACQRQK | KVTFDRLQVL | DSHYQDVLKE | VKAAASKVKA |
| 101 | NLLSVEEACS | LTPPHSAKSK | FGYGAKDVRC | HARKAVAHIN | SVWKDLLEDS |
| 151 | VTPIDTTIMA | KNEVFCVQPE | KGGRKPARLI | VFPDLGVRVC | EKMALYDVVS |
| 201 | KLPLAVMGSS | YGFQYSPGQR | VEFLVQAWKS | KKTPMGFSYD | TRCFDSTVTE |
| 251 | SDIRTEEAIY | QCCDLDPQAR | VAIKSLTERL | YVGGPLTNSR | GENCGYRRCR |
| 301 | ASGVLTTSCG | NTLTCYIKAR | AACRAAGLQD | CTMLVCGDDL | VVICESAGVQ |
| 351 | EDAASLRAFT | EAMTRYSAPP | GDPPQPEYDL | ELITSCSSNV | SVAHDGAGKR |
| 401 | VYYLTRDPTT | PLARAAWETA | RHTPVNSWLG | NIIMFAPTLW | ARMILMTHFF |
| 451 | SVLIARDQLE | QALNCEIYGA | CYSIEPLDLP | PIIQRLHGLS | AFSLHSYSPG |
| 501 | EINRVAACLR | KLGVPPLPAW | RHRARSVRAR | LLSRGGRAAI | CGKYLFNWAV |
| 551 | RTKLKLTPIA | AAGRLDLSGW | FTAGYSGGDI | YHSVSHARPR | |

Like other positive strand RNA viruses, HCV encodes an RNA-dependent RNA polymerase contained within the NS5B region. See, e.g., Beherns, et al., *EMBO J.* 15: 12–22 (1996); Hwang, et al., *Virology* 227: 439–446 (1997); Yuan, et al., *Biochem. Biophys. Res. Comm.* 232: 231–235 (1997). HCV NS5B catalyzes phosphodiester bond formation resulting in new RNA molecules which are then packaged into progeny virions. Like the RNA-dependent polymerases of other positive strand RNA viruses, HCV NS5B is a membrane-associated protein Hwang, et al., supra. Expression of the full-length NS5B region in recombinant systems, baculovirus or *E. coli*, for example, results in a protein which is membrane-associated or insoluble. See, e.g., Beherns, et al., supra; Hwang, et al., supra; Yuan, et al., supra. Although the overall amino acid composition of HCV NS5B is not hydrophobic, there is a 21-amino acid residue hydrophobic tail that could potentially serve as a membrane anchor region. This hydrophobic tail is found in other genotypes of HCV (see Table 4), as well as other members of the Flaviviridae family, such as the pestiviruses (e.g., bovine viral diarrhea virus and classic swine fever virus).

TABLE 3

Alignment of the carboxy-terminus of NS5B sequences from various HCV genotypes.

|  | 3001 | | | 3050 | |
|---|---|---|---|---|---|
| Hcv_2c | RLLDLSSWFT | VSAGGGDIYH | SVSRARPRLL | LLGLLLLCVG VGIFLLPAR. | (SEQ ID NO:5) |
| Hcv_J6 | RLLDLSSWFT | VGAGGGDIYH | SVSRARPRLL | LLGLLLLFVG VGLFLLPAR. | (SEQ ID NO:6) |
| Hcv_J8 | SRLDLSGWFT | VGAGGGDIYH | SVSHARPRLL | LLCLLLLSVG VGIFLLPAR. | (SEQ ID NO:7) |
| Hcv_H | GRLDLSGWFT | AGYSGGDIYH | SVSHARPRWF | WFCLLLLAAG VGIYLLPNR. | (SEQ ID NO:8) |

TABLE 3-continued

Alignment of the carboxy-terminus of NS5B sequences from various HCV genotypes.

```
Hcv_Rice GRLDLSGWFT AGYSGGDIYH SVSHARPRWF WFCLLLLAAG VGIYLLPNR.           (SEQ ID NO:9)

Hcv_1    GQLDLSGWFT AGYSGGDIYH SVSHARPRWI WFCLLLLAAG VGIYLLPNR.           (SEQ ID NO:10)

Hcv_J1   GRLDLSGWFT AGYSGGDIYH SVSHARPRWF WFCLLLLAAG VGIYLLPNR.           (SEQ ID NO:11)

Hcv_Klr3 SQLDLSSWFV AGYSGGDIYH SLSRARPRWF MWCLLLLSVG VGIYLLPNR.           (SEQ ID NO:12)

Hcv_Kls3 SQLDLSSWFV AGYSGGDIYH SLSRARPRWF MWCLLLLSVG VGIYLLPNR.           (SEQ ID NO:13)

Hcv_Klr1 SQLDLSNWFV AGYSGGDVYH SLSRARPRWF MLCLLLLSVG VGIYLLPNR.           (SEQ ID NO:14)

Hcv_Kls1 SQLDLSNWFV AGYSGGDVYH SLSRARPRWF MLCLLLLSVG VGIYLLPNR.           (SEQ ID NO:15)

Hcv_T    SQLDLSKWFV AGYGGGDIYH SLSRARPRWF MLCLLLLSVG VGIYLLPNR*           (SEQ ID NO:16)

Hcv_Bk   SRLDLSGWFV AGYSGGDIYH SLSRARPRWF MLCLLLLSVG VGIYLLPNR*           (SEQ ID NO:17)

Hcv_Hb   SRLDLSGWFV AGYSGGDIYH SLSRARPRWF MLCLLLLSVG VGIYLLPNR.           (SEQ ID NO:18)

Hcv_J483 SQLDLSGWFV AGYSGGDIYH SLSRARPRWF LLCLLLLSVG VGIYLLPNR.           (SEQ ID NO:19)

Hcv_J491 SQLDLSGWFV AGYSGGDIYH SLSRARPRWF PLCLLLLFVG VGIYLLPNR*           (SEQ ID NO:20)

Hcv_J    SQLDLSGWFV AGYNGGDIYH SLSRARPRWF MLCLLLLSVG VGIYLLPNR*           (SEQ ID NO:21)

Hcv_C2   SRLDLSGWFV AGYGGGDIYH SLSRARPRWF MLCLLLLSVG VGIYLLPNR*           (SEQ ID NO:22)

Hcv_Klr2 SQLDLSGWFV AGYSGGDIYH SVSRARPRWF MWCLLLLSVG VGIYLLPNR.           (SEQ ID NO:23)

Hcv_Kls2 SQLDLSGWFV AGYSGGDIYH SVSRARPRWF MWCLLLLSVG VGIYLLPNR.           (SEQ ID NO:24)

Hcv_Jt   SQLDLSSWFV AGYSGGDIYH SLSRARPRWF MWCLLLLSVG VGIYLLPNR.           (SEQ ID NO:25)

Hcv_Pp   SQLDLSGWFV AGYSGGDIYH SLSRARPRWF MWCLLLLSVG VGIYLLPNR.           (SEQ ID NO:26)

Hcv_Jk1  SQLDLSGWFV AGYSGGDIYH SLSRARPRWF MWCLLLLSVG VGIYLLPNR*           (SEQ ID NO:27)

Hcv_L1   SRLDLSGWFV AGYSGGDIYH SLSRARPRWF MLCLLLLSVG VGIYLLPNR*           (SEQ ID NO:28)

Hcv_L2   SRLDLSSWFV AGYSGGDIYH SVSHARPRWF MLCLLLLSVG VGIYLLPNR*           (SEQ ID NO:29)

Hcv_N    SQLDLSGWFV AGYSGGDIYH SLSRARPRWF MLCLLLLSVG VGIYLLPNR*           (SEQ ID NO:30)

Hcv_3a   GQLDLSSWFT VGVGGNDIYH SVSRARTRYL LLCLLLLTVG VGIFLLPAR.           (SEQ ID NO:31)

Hcv_3b   GQLDLSSWFT VGVGGNDIYH SVSRARTRHL LLCLLLLTVG VGIFLLPAR.           (SEQ ID NO:32)

BVDV(NADL)LQGKHYEQLQ LRTETNPVMG VGTERYKLGP IVNLLLRRLK ILLMTAVGVSS        (SEQ ID NO:33)

CSFV     GRHYEEL VLARKQFNNF QGTDRYNLGP IVNMVLRRLR VMMMTLIGRGV            (SEQ ID NO:34)
```

Deletion of this hydrophobic tail of HCV NS5B releases the protein into the soluble portion of the cell, allowing for a greater recovery of soluble protein for screening for inhibitors of NS5B enzymatic activity. Additionally, soluble protein produced in this method would allow for determination of the structure of the protein via x-ray crystallography or other methods that are well known in the art. This information could be used to discover or to guide the development of inhibitors. These inhibitors of NS5B potentially could have antiviral activity and, thus, could be used as therapeutic agents for the treatment of viruses of the Flaviviridae family, particularly HCV; flaviviruses such as yellow fever virus; Dengue virus types 1–4; and pestiviruses, such as bovine viral diarrhea virus and classic swine fever, among others.

Polypeptides

The polypeptides of the invention include the polypeptide of Table 3 [SEQ ID NO:4] (in particular the mature polypeptide) as well as polypeptides and fragments, particularly those which have the biological activity of HCV NS5B, and also those which have at least 70% identity to the polypeptide of Table 3 [SEQ ID NO:4] or the relevant portion, preferably at least 80% identity to the polypeptide of Table 3 [SEQ ID NO:4], and more preferably at least 90% similarity (more preferably at least 90% identity) to the polypeptide of Table 3 [SEQ ID NO:4] and still more preferably at least 95% similarity (still more preferably at least 95% identity) to the polypeptide of Table 3 [SEQ ID NO:4] and also include portions of such polypeptides with such portion of the polypeptide generally containing at least 30 amino acids and, more preferably, at least 50 amino acids.

A fragment is a variant polypeptide having an amino acid sequence that entirely is the same as part but not all of the amino acid sequence of the aforementioned polypeptides. As with HCV NS5B polypeptides, fragments may be "free-standing," or comprised within a larger polypeptide of which they form a part or region, most preferably as a single continuous region, a single larger polypeptide.

Preferred fragments include, for example, variants of the amino acid sequence of Table 3 [SEQ ID NO:4], thereof, such as a continuous series of residues that includes the amino terminus, or a continuous series of residues that includes the carboxyl terminus. Degradation forms of the polypeptides of the invention in a host cell are also preferred. Further preferred are fragments characterized by structural or functional attributes, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments, which are those fragments that mediate activities of HCV NS5B, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of HCV or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides

Another aspect of the invention relates to isolated polynucleotides, including the full length gene, that encode the HCV NS5B polypeptide having the deduced amino acid sequence of Table 3 [SEQ ID NO:3] and polynucleotides closely related thereto and variants thereof.

Using the information provided herein, a polynucleotide of the invention encoding the HCV NS5B polypeptide set forth in Table 3 [SEQ ID NO:3], may be obtained using standard cloning and screening methods, such as those for cloning and sequencing chromosomal DNA fragments from bacteria using HCV NS5B cells as starting material, followed by obtaining a full length clone. For example, to obtain a polynucleotide sequence of the invention encoding the polypeptide sequence given in Table 3 [SEQ ID NO:4], typically a library of clones of chromosomal DNA of HCV NS5B in E. coli or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence, it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook, et al., MOLECULAR CLONING, A LABORATORY MANUAL, 2nd Ed.; Cold Spring Harbor Laboratory Press, Cold Spring Harbor, New York (1989). (See, in particular, Screening By Hybridization 1.90 and Sequencing Denatured Double-Stranded DNA Templates 13.70). Illustrative of the invention, the polynucleotide encoding the polypeptide set out in Table 3 [SEQ ID NO:4] was discovered in a DNA library derived from HCV NS5B.

The DNA sequence of HCV NS5B contains an open reading frame encoding a protein having about the number of amino acid residues set forth in Table 2 [SEQ ID NO: 2] with a deduced molecular weight that can be calculated using amino acid residue molecular weight values well known in the art. The polynucleotide of SEQ ID NO: 1 encodes the polypeptide of SEQ ID NO: 2.

The invention provides a polynucleotide sequence identical over its entire length to a sequence encoding the sequence in Table 3 [SEQ ID NO:3]. Also provided by this invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz, et al., *Proc. Natl. Acad. Sci., USA* 86: 821–824 (1989), or an HA tag (Wilson, et al., *Cell* 37: 767 (1984). Polynucleotides of the invention also include, but are not limited to, polynucleotides comprising a structural gene and its naturally associated sequences that control gene expression.

A preferred embodiment of the invention is the polynucleotide set forth in SEQ ID NO:3 of Table 3, which encodes a HCV NS5B polypeptide.

The term "polynucleotide encoding a polypeptide" as used herein encompasses polynucleotides that include a sequence encoding a polypeptide of the invention, particularly a viral polypeptide and more particularly a polypeptide of HCV NS5B having the amino acid sequence set out in Table 3 [SEQ ID NO:4]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table 3 [SEQ ID NO:4]. Variants that are fragments of the polynucleotides of the invention may be used to synthesize full-length polynucleotides of the invention.

Further particularly preferred embodiments are polynucleotides encoding HCV NS5B variants, that have the amino acid sequence of HCV NS5B polypeptide of Table 3 [SEQ ID NO:4] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of HCV NS5B.

Further preferred embodiments of the invention are polynucleotides that are at least 70% identical over their entire length to a polynucleotide encoding HCV NS5B polypeptide having the amino acid sequence set out in Table 3 [SEQ ID NO:4], and polynucleotides that are complementary to such polynucleotides. Alternatively, most highly preferred are polynucleotides that comprise a region that is at least 80% identical over its entire length to a polynucleotide encoding HCV NS5B polypeptide and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 3 [SEQ ID NO:3].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 micrograms/ml denatured, sheared salmon sperm DNA, followed by washing the hybridization support in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence encoding the polypeptide sequence set forth in SEQ ID NO:4 under stringent hybridization conditions with a probe having the sequence of said polynucleotide sequence or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding HCV NS5B and to isolate cDNA and genomic clones of other genes that have a high sequence similarity to the HCV NS5B gene. Such probes generally will comprise at least 15 bases. Preferably, such probes will have at least 30 bases and may have at least 50 bases. Particularly preferred probes will have at least 30 bases and will have 50 bases or less.

For example, the coding region of the truncated HCV NS5B gene may be isolated by screening using the DNA sequence provided in SEQ ID NO:3 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of SEQ ID NOs:3 and/or 4 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed, such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as *streptococci, staphylococci, enterococci, E. coli, streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293, hepatic cells, and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook, et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the HCV NS5B polynucleotides of the invention for use as diagnostic reagents. Detection of HCV NS5B in a eukaryote, particularly a mammal, and especially a human, will provide a diagnostic method for diagnosis of a disease. Eukaryotes (herein also "individual(s)"), particularly mammals, and especially humans, particularly those infected or suspected to be infected with an organism comprising the HCV NS5B gene may be detected at the nucleic acid level by a variety of techniques.

Nucleic acids for diagnosis may be obtained from a bodily sample of an infected individual. Such a bodily sample can be either cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled HCV NS5B polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers, et al., *Science,* 230: 1242 (1985). Sequence changes at specific locations also may be revealed by nuclease protection assays, such as RNase and S1 protection or a chemical cleavage method. See, e.g., Cotton, et al., *Proc. Natl. Acad. Sci., USA,* 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding HCV NS5B can be used to identify and analyze mutations.

The invention further provides a process for diagnosing disease, preferably viral infections linked to the Flaviviridae family, particularly HCV; flaviviruses such as yellow fever virus; Dengue virus types 1–4; and pestiviruses, such as bovine viral diarrhea virus and classic swine fever, among others, comprising determining from a sample derived from an individual a increased level of expression of HCV NS5B polynucleotide having the sequence of Table 3 [SEQ ID NO:3]. Increased or decreased expression of HCV NS5B polynucleotide can be measured using any one of the methods well known in the art for the quantitation of polynucleotides, such as, for example, amplification, PCR, RT-PCR, RNase protection, Northern blotting and other hybridization methods.

In addition, a diagnostic assay in accordance with the invention for detecting over-expression of HCV NS5B protein compared to normal control tissue samples may be used to detect the presence of an infection, for example. Assay techniques that can be used to determine levels of an HCV NS5B protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, et al., *Nature* 256: 495–497 (1975); Kozbor, et al., *Immunology Today* 4: 72 (1983); Cole, et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively, phage display technology may be utilized to select antibody genes with binding activities towards the polypeptide either from repertoires of PCR amplified v-genes of lymphocytes from humans screened for possessing anti-HCV NS5B or from naive libraries (McCafferty, et al., (1990), Nature 348: 552–554; Marks, et al., (1992) Biotechnology 10: 779–783). The affinity of these antibodies can also be improved by chain shuffling (Clackson, et al., (1991) Nature 352: 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against HCV NS5B polypeptide may be employed to treat viral infections, preferably viruses of the Flaviviridae family, particularly HCV; flaviviruses such as yellow fever virus; Dengue virus types 1–4; and pestiviruses, such as bovine viral diarrhea virus, and classic swine fever, among others.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarily determining region(s) of the hybridoma-derived antibody has been transplanted into a human monoclonal antibody, for example as described in Jones, et al., Nature 321: 522–525 (1986), or Tempest, et al., Biotechnology 9: 266–273 (1991).

The use of a polynucleotide of the invention in genetic immunization will preferably employ a suitable delivery method such as direct injection of plasmid DNA into muscles (Wolff, et al., Hum. Mol. Genet. 1: 363 (1992), Manthorpe, et al., Hum. Gene Ther. 4: 419 (1963)), delivery of DNA complexed with specific protein carriers (Wu, et al., J. Biol. Chem. 264: 16985 (1989)), coprecipitation of DNA with calcium phosphate (Benvenisty & Reshef, Proc. Natl. Acad. Sci. USA, 83: 9551 (1986)), encapsulation of DNA in various forms of liposomes (Kaneda, et al., Science 243: 375 (1989)), particle bombardment (Tang, et al., Nature 356: 152 (1992), Eisenbraun, et al., DNA Cell Biol. 12:791 (1993)) and in vivo infection using cloned retroviral vectors (Seeger, et al., Proc. Natl. Acad. Sci. USA 81: 5849 (1984)).

Antagonists and Agonists—Assays and Molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan, et al., Current Protocols in Immunology 1(2): Chapter 5 (1991).

The present invention also provides a method of screening compounds to identify those which enhance (agonist) or block (antagonist) the action of HCV NS5B polypeptides or polynucleotides, particularly those compounds that are virustatic. The method of screening may involve high-throughput techniques. For example, to screen for agonists or antagonists, a synthetic reaction mix, a viral fragment or component, or a preparation of any thereof, comprising HCV NS5B polypeptide (SEQ ID NO:4) and a labeled substrate or ligand of such polypeptide is incubated in the absence or the presence of a candidate molecule that may be an HCV NS5B agonist or antagonist. The ability of the candidate molecule to agonize or antagonize the HCV NS5B polypeptide (SEQ ID NO:4) is reflected in decreased binding of the labeled ligand or decreased production of product from such substrate. Molecules that bind gratuitously, i.e., without inducing the effects of HCV NS5B polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in HCV NS5B polynucleotide or polypeptide activity, and binding assays known in the art.

Another example of an assay for HCV NS5B antagonists is a competitive assay that combines HCV NS5B (SEQ ID NO:4) and a potential antagonist with HCV NS5B-binding molecules, recombinant HCV NS5B binding molecules, natural substrates or ligands, or substrate or ligand mimetics, under appropriate conditions for a competitive inhibition assay. HCV NS5B (SEQ ID NO:4) can be labeled, such as by radioactivity or a colorimetric compound, such that the number of HCV NS5B molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing HCV NS5B-induced activities, thereby preventing the action of HCV NS5B by excluding HCV NS5B from binding.

Potential antagonists include a small molecule that binds to and occupies the binding site of the polypeptide thereby preventing binding to cellular binding molecules, such that normal biological activity is prevented. Examples of small molecules include, but are not limited to, small organic molecules, peptides or peptide-like molecules. Other potential antagonists include antisense molecules. See Okano, J. Neurochem. 56: 560 (1991); OLIGODEOXYNUCLE-OTIDES AS ANTISENSE INHIBITORS OF GENE EXPRESSION, CRC Press, Boca Raton, Fla. (1988), for a description of these molecules. Preferred potential antagonists include compounds related to and variants of HCV NS5B.

The DNA sequences encoding the HCV NS5B polypeptides provided herein may be used in the discovery and development of antibacterial compounds. The encoded protein, upon expression, can be used as a target for the screening of antiviral drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular, the molecules of the invention may be used: in the prevention of adhesion of virus particles, to mammalian extracellular matrix proteins on in-dwelling devices or to extracellular matrix proteins in wounds; to block HCV NS5B protein-mediated mammalian cell invasion by, for example, initiating phosphorylation of mammalian tyrosine kinases (Rosenshine, et al., *Infect. Immun.* 60: 2211 (1992); to block viral adhesion between mammalian extracellular matrix proteins and viral HCV NS5B proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat viruses linked to the Flaviviridae family, particularly HCV; flaviviruses such as yellow fever virus; Dengue virus types 1–4; and pestiviruses, such as bovine viral diarrhea virus and classic swine fever, among others.

Vaccines

Another aspect of the invention relates to a method for inducing an immunological response in an individual, particularly a mammal which comprises inoculating the individual with HCV NS5B (SEQ ID NO:4), or a fragment or variant thereof, adequate to produce antibody and/or T cell immune response to protect said individual from infection, particularly viral infection and, most particularly, HCV infection. Also provided are methods whereby such immunological response slows bacterial replication. Yet another aspect of the invention relates to a method of inducing immunological response in an individual which comprises delivering to such individual a nucleic acid vector to direct expression of HCV NS5B, or a fragment or a variant thereof, for expressing HCV NS5B, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to HCV NS5B, wherein the composition comprises a recombinant HCV NS5B or protein coded therefrom comprising DNA which codes for and expresses an antigen of said HCV NS5B or protein coded therefrom. The immunological response may be used therapeutically or prophylactically and may take the form of antibody immunity or cellular immunity such as that arising from CTL or CD4+ T cells.

An HCV NS5B polypeptide or a fragment thereof may be fused with co-protein which may not by itself produce antibodies, but is capable of stabilizing the first protein and producing a fused protein which will have immunogenic and protective properties. Thus, fused recombinant protein, preferably further comprises an antigenic co-protein, such as lipoprotein D from Hemophilus influenzae, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, et al. *Science* 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with HCV will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly HCV infection, in mammals, particularly humans.

The polypeptide may be used as an antigen for vaccination of a host to produce specific antibodies which protect against invasion of viruses, for example by blocking adherence of viruses to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation insotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to HCV NS5B protein, it is to be understood that fragments of the naturally occurring protein and similar proteins with additions, deletions or substitutions which do not substantially affect the immunogenic properties of the recombinant protein are contemplated within the scope of the invention.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the pharmaceutical composition may be administered to an individual as an injectable composition, for example as a sterile aqueous dispersion, preferably isotonic.

Alternatively, the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially HCV wound infections.

Alternatively, the composition of the invention may be used to bathe an indwelling device immediately before insertion. The polypeptides or other compounds of this invention will preferably be present at a concentration of 1 mg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

EXAMPLES

Biological Methods

Example 1
Preparation of HCV NS5B Truncation Mutant

The HCV NS5B region (SEQ ID NO:2) was cloned into a bacterial expression vector pET-15b (Novagen) such that an initiating methionine and hexahistidine tag was added to the amino terminus of the protein to generate pLG65. Two additional plasmids were made in which either the 21 carboxy-terminal amino acids of HCV NS5B were deleted or replaced by a Flag epitope tag (Hopp, et al., *Biotechnology* 6: 1205–1210 (1988)), which is a hydrophilic stretch of amino acids. NS5B expression constructs were transferred into the *E. coli* strain BL21(DE3), and the NS5B proteins were induced by addition of IPTG using standard methods. Bacteria were harvested, and lysed by sonication three times for 30 seconds in extraction buffer (20 mM Tris, pH 7.5, 20% glycerol, 200 mM NaCl, 1 mM EDTA, 10 mM dithiothreitol, 10 mgs/ml lysozyme, and a protease inhibitor cocktail (COMPLETE tabs from Behringer Mannheim).

Example 2
HCV NS5B Truncation Mutant Has Improved Solubility Over Full-Length HCV NS5B Protein Some of the material generated in Example 1 was reserved as a sample of the total protein (T). The sample was centrifuged at 14,000 rpm at 4° C. in a Eppendorf 5415C microfuge for fifteen minutes. The supernatant (S1) was removed and spun for 30 minutes at 4° C. at 100,000×g. The supernatant (S2) from this spin represented the truly soluble material. Equal amounts of protein from were analyzed for each clone from each sample (T, S1, S2) were analyzed by SDS-containing polyacrylamide gel electrophoresis, followed by western blotting using standard procedures. HCV NS5B was detected using a rabbit polyclonal antisera which had been generated using a peptide derived from the NS5B region (amino acids 385–403 of HCV NS5B (SEQ ID NO:2)) coupled to keyhole limpet hemocyanin (KLH). Results show that the truncated HCV NS5B proteins in which the carboxy terminal 21 amino acids were either deleted or replaced by the Flag epitope tag sequence were present in the soluble fraction (S2) in far greater amounts when compared with the full length NS5B protein which was either barely detectable or absent in the soluble fraction (S2).

All publications including, but not limited to, patents and patent applications, cited in this specification, are herein incorporated by reference as if each individual publication were specifically and individually indicated to be incorporated by reference herein as though fully set forth.

The above description fully discloses the invention, including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. A method of identifying compounds which inhibit or which activate the RNA-dependent RNA polymerase activity of the HCV NS5B polypeptide, comprising:

(a) contacting a composition comprising the polypeptide of SEQ ID NO: 4 with a candidate compound to be screened under conditions to permit interaction between said compound and the polypeptide; and (b) determining whether said compound activates or inhibits the RNA-dependent RNA polymerase activity of the polypeptide of SEQ ID NO: 4.

2. The method according to claim 1 wherein the composition of step (a) further comprises a second component that provides a detectable signal in response to the interaction of said polypeptide with said compound, and wherein step (b) is achieved by detecting the level of the signal generated in step (a).

* * * * *

SEQUENCE LISTING

<160> NUMBER OF SEQ ID NOS: 34

<210> SEQ ID NO: 1
<211> LENGTH: 1710
<212> TYPE: DNA
<213> ORGANISM: Viral

<400> SEQUENCE: 1

```
tcaatgtctt atacctggac aggcgcactc gtcacccgt  gcgctgcgga agaacaaaaa      60
ctgcccatca acgcactgag caactcgttg ctacgccatc acaatctggt atattccacc     120
acttcacgca gtgcttgcca aaggcagaag aaagtcacat tgacagact  gcaagttctg     180 gacagccatt accaggacgt gctcaaggag gtcaaagcag cggcgtcaaa agtgaaggct     240
aacttgctat ccgtagagga agcttgcagc ctgacgcccc cacattcagc caaatccaag     300
tttggctatg gggcaaaaga cgtccgttgc catgccagaa aggccgtagc ccacatcaac     360
tccgtgtgga aagaccttct ggaagacagt gtaacaccaa tagacactat catcatggcc     420
aagaacgagg tcttctgcgt tcagcctgag aagggggtc  gtaagccagc tcgtctcatc     480
gtgttccccg acctgggcgt gcgcgtgtgc gagaagatgg ccctgtacga cgtggttagc     540
aaactccccc tggccgtgat gggaagctcc tacggattcc aatactcacc aggacagcgg     600
gttgaattcc tcgtgcaagc gtggaagtcc aagaagaccc cgatggggtt cccgtatgat     660
acccgctgtt ttgactccac agtcactgag agcgacatcc gtacggagga ggcaatttac     720
caatgttgtg acctggaccc ccaagcccgc gtggccatca agtccctcac tgagaggctt     780
tatgttgggg gccctcttac caattcaagg ggggaaaact gcggctatcg caggtgccgc     840
gcgagcggcg tactgacaac tagctgtggt aacaccctca cttgctacat caaggcccgg     900
gcagcccgtc gagccgcagg gctccaggac tgcaccatgc tcgtgtgtgg cgacgactta     960
gtcgttatct gtgaaagtgc gggggtccag gaggacgcgg cgagcctgag agcctttacg    1020
gaggctatga ccaggtactc cgccccccc  ggggaccccc cacaaccaga atacgacttg    1080
gagcttataa catcatgctc ctccaacgtg tcagtcgccc acgacggcgc tggaaaaagg    1140
gtctactacc ttacccgtga ccctacaacc ccctcgcga gagccgcgtg ggagacagca    1200
agacacactc cagtcaattc ctggctaggc aacataatca tgtttgcccc cacactgtgg    1260
gcgaggatga tactgatgac ccatttcttt agcgtcctca tagccaggga tcagcttgaa    1320
caggctctta ctgtgagat  ctacgcagcc tgctactcca tagaaccact ggatctacct    1380
ccaatcattc aaagactcca tggcctcagc gcattttta  tccacagtta ctctccaggt    1440
```

-continued

```
gaagtcaata gggtggccgc atgcctcaga aaacttgggg tcccgcccett gcgagcttgg    1500 agacaccggg cccggagcgt ccgcgctagg cttctgtcca ggggaggcag ggctgccata    1560
tgtggcaagt acctcttcaa ctgggcagta agaacaaagc tcaaactcac tccaatagcg    1620
gccgctggcc ggctggactt gtccggttgg ttcacggctg gctacagcgg gggagacatt    1680
tatcacagcg tgtctcatgc ccggccccgc                                    1710
```

<210> SEQ ID NO: 2
<211> LENGTH: 591
<212> TYPE: PRT
<213> ORGANISM: Viral

<400> SEQUENCE: 2

```
Ser Met Ser Tyr Thr Trp Thr Gly Ala Leu Val Thr Pro Cys Ala Ala
 1               5                  10                  15

Glu Glu Gln Lys Leu Pro Ile Asn Ala Leu Ser Asn Ser Leu Leu Arg
            20                  25                  30

His His Asn Leu Val Tyr Ser Thr Thr Ser Arg Ser Ala Cys Gln Arg
        35                  40                  45

Gln Lys Lys Val Thr Phe Asp Arg Leu Gln Val Leu Asp Ser His Tyr
    50                  55                  60

Gln Asp Val Leu Lys Glu Val Lys Ala Ala Ser Lys Val Lys Ala
65                  70                  75                  80

Asn Leu Leu Ser Val Glu Glu Ala Cys Ser Leu Thr Pro Pro His Ser
                85                  90                  95

Ala Lys Ser Lys Phe Gly Tyr Gly Ala Lys Asp Val Arg Cys His Ala
           100                 105                 110

Arg Lys Ala Val Ala His Ile Asn Ser Val Trp Lys Asp Leu Leu Glu
       115                 120                 125

Asp Ser Val Thr Pro Ile Asp Thr Thr Ile Met Ala Lys Asn Glu Val
   130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Lys Leu Pro Leu Ala Val Met Gly Ser Ser Tyr Gly
           180                 185                 190

Phe Gln Tyr Ser Pro Gly Gln Arg Val Glu Phe Leu Val Gln Ala Trp
       195                 200                 205

Lys Ser Lys Lys Thr Pro Met Gly Phe Ser Tyr Asp Thr Arg Cys Phe
   210                 215                 220

Asp Ser Thr Val Thr Glu Ser Asp Ile Arg Thr Glu Glu Ala Ile Tyr
225                 230                 235                 240

Gln Cys Cys Asp Leu Asp Pro Gln Ala Arg Val Ala Ile Lys Ser Leu
                245                 250                 255

Thr Glu Arg Leu Tyr Val Gly Gly Pro Leu Thr Asn Ser Arg Gly Glu
           260                 265                 270

Asn Cys Gly Tyr Arg Arg Cys Arg Ala Ser Gly Val Leu Thr Thr Ser
       275                 280                 285

Cys Gly Asn Thr Leu Thr Cys Tyr Ile Lys Ala Arg Ala Ala Cys Arg
   290                 295                 300

Ala Ala Gly Leu Gln Asp Cys Thr Met Leu Val Cys Gly Asp Asp Leu
305                 310                 315                 320

Val Val Ile Cys Glu Ser Ala Gly Val Gln Glu Asp Ala Ala Ser Leu
```

```
                    325                 330                 335
Arg Ala Phe Thr Glu Ala Met Thr Arg Tyr Ser Ala Pro Pro Gly Asp
                340                 345                 350
Pro Pro Gln Pro Glu Tyr Asp Leu Glu Leu Ile Thr Ser Cys Ser Ser
            355                 360                 365
Asn Val Ser Val Ala His Asp Gly Ala Gly Lys Arg Val Tyr Tyr Leu
        370                 375                 380
Thr Arg Asp Pro Thr Thr Pro Leu Ala Arg Ala Ala Trp Glu Thr Ala
385                 390                 395                 400
Arg His Thr Pro Val Asn Ser Trp Leu Gly Asn Ile Ile Met Phe Ala
                405                 410                 415
Pro Thr Leu Trp Ala Arg Met Ile Leu Met Thr His Phe Phe Ser Val
                420                 425                 430
Leu Ile Ala Arg Asp Gln Leu Glu Gln Ala Leu Asn Cys Glu Ile Tyr
                435                 440                 445
Gly Ala Cys Tyr Ser Ile Glu Pro Leu Asp Leu Pro Pro Ile Ile Gln
        450                 455                 460
Arg Leu His Gly Leu Ser Ala Phe Ser Leu His Ser Tyr Ser Pro Gly
465                 470                 475                 480
Glu Ile Asn Arg Val Ala Ala Cys Leu Arg Lys Leu Gly Val Pro Pro
                485                 490                 495
Leu Arg Ala Trp Arg His Arg Ala Arg Ser Val Arg Ala Arg Leu Leu
                500                 505                 510
Ser Arg Gly Gly Arg Ala Ala Ile Cys Gly Lys Tyr Leu Phe Asn Trp
            515                 520                 525
Ala Val Arg Thr Lys Leu Lys Leu Thr Pro Ile Pro Ala Ala Gly Arg
        530                 535                 540
Leu Asp Leu Ser Gly Trp Phe Thr Ala Gly Tyr Ser Gly Gly Asp Ile
545                 550                 555                 560
Tyr His Ser Val Ser His Ala Arg Pro Arg Trp Phe Trp Phe Cys Leu
                565                 570                 575
Leu Leu Leu Ala Ala Gly Val Gly Ile Tyr Leu Leu Pro Asn Arg
                580                 585                 590

<210> SEQ ID NO: 3
<211> LENGTH: 1710
<212> TYPE: DNA
<213> ORGANISM: Viral

<400> SEQUENCE: 3
tcaatgtctt attcctggac aggcgcactc gtcaccccgt gcgctgcgga agaacaaaaa      60
ctgcccatca acgcactgag caactcgttg ctacgccatc acaatctggt gtattccacc     120
acttcacgca gtgcttgcca aaggcagaag aaagtcacat ttgacagact gcaagttctg     180
gacagccatt accaggacgt gctcaaggag gtcaaagcag cggcgtcaaa agtgaaggct     240
aacttgctat ccgtagagga agcttgcagc ctgacgcccc cacattcagc caaatccaag     300
tttggctatg gggcaaaaga cgtccgttgc catgccagaa aggccgtagc ccacatcaac     360
tccgtgtgga aagaccttct ggaagacagt gtaacaccaa tagacactac catcatggcc     420
aagaacgagg ttttctgcgt tcagcctgag aaggggggtc gtaagccagc tcgtctcatc     480
gtgttccccg acctgggcgt gcgcgtgtgc gagaagatgg ccctgtacga cgtggttagc     540
aagctccccc tggccgtgat gggaagctcc tacggattcc aatactcacc aggacagcgg     600
gttgaattcc tcgtgcaagc gtggaagtcc aagaagaccc cgatggggtt ctcgtatgat     660
```

-continued

```
acccgctgtt ttgactccac agtcactgag agcgacatcc gtacggagga ggcaatttac    720
caatgttgtg acctggaccc ccaagcccgc gtggccatca agtccctcac tgagaggctt    780
tatgttgggg gccctcttac caattcaagg ggggaaaact gcggctaccg caggtgccgc    840
gcgagcggcg tactgacaac tagctgtggt aacaccctca cttgctacat caaggcccgg    900
gcagcctgtc gagccgcagg gctccaggac tgcaccatgc tcgtgtgtgg cgacgactta    960
gtcgttatct gtgaaagtgc gggggtccag gaggacgcgg cgagcctgag agccttcacg   1020
gaggctatga ccaggtactc cgccccccc ggggaccccc cacaaccaga atacgacttg    1080
gagcttataa catcatgctc ctccaacgtg tcagtcgccc acgacggcgc tggaaagagg   1140
gtctactacc ttacccgtga ccctacaacc cccctcgcga gagccgcgtg ggagacagca   1200
agacacactc cagtcaattc ctggctaggc aacataatca tgtttgcccc cacactgtgg   1260
gcgaggatga tactgatgac ccatttcttt agcgtcctca tagccaggga tcagcttgaa   1320
caggctctta actgtgagat ctacggagcc tgctactcca tagaaccact ggatctacct   1380
ccaatcattc aaagactcca tggcctcagc gcatttttcac tccacagtta ctctccaggt   1440
gaaatcaata gggtggccgc atgcctcaga aaacttgggg tcccgcccct tgcgagcttgg   1500 agacaccggg cccggagcgt ccgcgctagg cttctgtcca gaggaggcag ggctgccata   1560
tgtggcaagt acctcttcaa ctgggcagta agaacaaagc tcaaactcac tccaatagcg   1620 ccgctggcc ggctggactt gtccggttgg ttcacggctg gctacagcgg gggagacatt   1680
tatcacagcg tgtctcatgc ccggcccccgc                                    1710
```

<210> SEQ ID NO: 4
<211> LENGTH: 590
<212> TYPE: PRT
<213> ORGANISM: Viral

<400> SEQUENCE: 4

```
Ser Met Ser Tyr Ser Trp Thr Gly Ala Leu Val Thr Pro Cys Ala Ala
1               5                   10                  15

Glu Glu Gln Lys Leu Pro Ile Asn Ala Leu Ser Asn Ser Leu Leu Arg
            20                  25                  30

His His Asn Leu Val Tyr Ser Thr Thr Ser Arg Ser Ala Cys Gln Arg
        35                  40                  45

Gln Lys Leu Arg His His Asn Leu Val Tyr Ser Thr Thr Ser Arg Ser
    50                  55                  60

Ala Cys Gln Arg Gln Lys Lys Val Thr Phe Asp Arg Leu Gln Val Leu
65                  70                  75                  80

Asp Ser His Tyr Gln Asp Val Leu Lys Glu Val Lys Ala Ala Ala Ser
                85                  90                  95

Lys Val Lys Ala Asn Leu Leu Ser Val Glu Glu Ala Cys Ser Leu Thr
            100                 105                 110

Pro Pro His Ser Ala Lys Ser Lys Phe Gly Tyr Gly Ala Lys Asp Val
        115                 120                 125

Arg Cys His Ala Arg Lys Ala Val Ala His Ile Asn Ser Val Trp Lys
    130                 135                 140

Asp Leu Leu Glu Asp Ser Val Thr Pro Ile Asp Thr Thr Ile Met Ala
145                 150                 155                 160

Lys Asn Glu Val Phe Cys Val Gln Pro Glu Lys Gly Gly Arg Lys Pro
                165                 170                 175

Ala Arg Leu Ile Val Phe Pro Asp Leu Gly Val Arg Val Cys Glu Lys
```

-continued

```
                180                 185                 190
Met Ala Leu Tyr Asp Val Val Ser Lys Leu Pro Leu Ala Val Met Gly
                195                 200                 205

Ser Ser Tyr Gly Phe Gln Tyr Ser Pro Gly Gln Arg Val Glu Phe Leu
210                 215                 220

Val Gln Ala Trp Lys Ser Lys Lys Thr Pro Met Gly Phe Ser Tyr Asp
225                 230                 235                 240

Thr Arg Cys Phe Asp Ser Thr Val Thr Glu Ser Asp Ile Arg Thr Glu
                245                 250                 255

Glu Ala Ile Tyr Gln Cys Cys Asp Leu Asp Pro Gln Ala Arg Val Ala
                260                 265                 270

Ile Lys Ser Leu Thr Glu Arg Leu Tyr Val Gly Gly Pro Leu Thr Asn
                275                 280                 285

Ser Arg Gly Glu Asn Cys Gly Tyr Arg Arg Cys Arg Ala Ser Gly Val
                290                 295                 300

Leu Thr Thr Ser Cys Gly Asn Thr Leu Thr Cys Tyr Ile Lys Ala Arg
305                 310                 315                 320

Ala Ala Cys Arg Ala Ala Gly Leu Gln Asp Cys Thr Met Leu Val Cys
                325                 330                 335

Gly Asp Asp Leu Val Val Ile Cys Glu Ser Ala Gly Val Gln Glu Asp
                340                 345                 350

Ala Ala Ser Leu Arg Ala Phe Thr Glu Ala Met Thr Arg Tyr Ser Ala
                355                 360                 365

Pro Pro Gly Asp Pro Pro Gln Pro Glu Tyr Asp Leu Glu Leu Ile Thr
                370                 375                 380

Ser Cys Ser Ser Asn Val Ser Val Ala His Asp Gly Ala Gly Lys Arg
385                 390                 395                 400

Val Tyr Tyr Leu Thr Arg Asp Pro Thr Thr Pro Leu Ala Arg Ala Ala
                405                 410                 415

Trp Glu Thr Ala Arg His Thr Pro Val Asn Ser Trp Leu Gly Asn Ile
                420                 425                 430

Ile Met Phe Ala Pro Thr Leu Trp Ala Arg Met Ile Leu Met Thr His
                435                 440                 445

Phe Phe Ser Val Leu Ile Ala Arg Asp Gln Leu Glu Gln Ala Leu Asn
450                 455                 460

Cys Glu Ile Tyr Gly Ala Cys Tyr Ser Ile Glu Pro Leu Asp Leu Pro
465                 470                 475                 480

Pro Ile Ile Gln Arg Leu His Gly Leu Ser Ala Phe Ser Leu His Ser
                485                 490                 495

Tyr Ser Pro Gly Glu Ile Asn Arg Val Ala Ala Cys Leu Arg Lys Leu
                500                 505                 510

Gly Val Pro Pro Leu Arg Ala Trp Arg His Arg Ala Arg Ser Val Arg
                515                 520                 525

Ala Arg Leu Leu Ser Arg Gly Gly Arg Ala Ala Ile Cys Gly Lys Tyr
                530                 535                 540

Leu Phe Asn Trp Ala Val Arg Thr Lys Leu Lys Leu Thr Pro Ile Ala
545                 550                 555                 560

Ala Ala Gly Arg Leu Asp Leu Ser Gly Trp Phe Thr Ala Gly Tyr Ser
                565                 570                 575

Gly Gly Asp Ile Tyr His Ser Val Ser His Ala Arg Pro Arg
                580                 585                 590
```

<210> SEQ ID NO: 5

```
<211> LENGTH: 49
<212> TYPE: PRT
<213> ORGANISM: Viral

<400> SEQUENCE: 5

Arg Leu Leu Asp Leu Ser Ser Trp Phe Thr Val Ser Ala Gly Gly Gly
1               5                   10                  15

Asp Ile Tyr His Ser Val Ser Arg Ala Arg Pro Arg Leu Leu Leu Leu
            20                  25                  30

Gly Leu Leu Leu Leu Cys Val Gly Val Gly Ile Phe Leu Leu Pro Ala
        35                  40                  45

Arg

<210> SEQ ID NO: 6
<211> LENGTH: 49
<212> TYPE: PRT
<213> ORGANISM: Viral

<400> SEQUENCE: 6

Arg Leu Leu Asp Leu Ser Ser Trp Phe Thr Val Gly Ala Gly Gly Gly
1               5                   10                  15

Asp Ile Tyr His Ser Val Ser Arg Ala Arg Pro Arg Leu Leu Leu Leu
            20                  25                  30

Gly Leu Leu Leu Leu Phe Val Gly Val Gly Leu Phe Leu Leu Pro Ala
        35                  40                  45

Arg

<210> SEQ ID NO: 7
<211> LENGTH: 49
<212> TYPE: PRT
<213> ORGANISM: Viral

<400> SEQUENCE: 7

Ser Arg Leu Asp Leu Ser Gly Trp Phe Thr Val Gly Ala Gly Gly Gly
1               5                   10                  15

Asp Ile Tyr His Ser Val Ser His Ala Arg Pro Arg Leu Leu Leu Leu
            20                  25                  30

Cys Leu Leu Leu Leu Ser Val Gly Val Gly Ile Phe Leu Leu Pro Ala
        35                  40                  45

Arg

<210> SEQ ID NO: 8
<211> LENGTH: 50
<212> TYPE: PRT
<213> ORGANISM: Viral

<400> SEQUENCE: 8

His Gly Arg Leu Asp Leu Ser Gly Trp Phe Thr Ala Gly Tyr Ser Gly
1               5                   10                  15

Gly Asp Ile Tyr His Ser Val Ser His Ala Arg Pro Arg Trp Phe Trp
            20                  25                  30

Phe Cys Leu Leu Leu Leu Ala Ala Gly Val Gly Ile Tyr Leu Leu Pro
        35                  40                  45

Asn Arg

<210> SEQ ID NO: 9
<211> LENGTH: 49
<212> TYPE: PRT
<213> ORGANISM: Viral
```

<400> SEQUENCE: 9

Gly Arg Leu Asp Leu Ser Gly Trp Phe Thr Ala Gly Tyr Ser Gly Gly
1               5                   10                  15

Asp Ile Tyr His Ser Val Ser His Ala Arg Pro Arg Trp Phe Trp Phe
            20                  25                  30

Cys Leu Leu Leu Ala Ala Gly Val Gly Ile Tyr Leu Leu Pro Asn
        35                  40                  45

Arg

<210> SEQ ID NO: 10
<211> LENGTH: 49
<212> TYPE: PRT
<213> ORGANISM: Viral

<400> SEQUENCE: 10

Gly Gln Leu Asp Leu Ser Gly Trp Phe Thr Ala Gly Tyr Ser Gly Gly
1               5                   10                  15

Asp Ile Tyr His Ser Val Ser His Ala Arg Pro Arg Trp Ile Trp Phe
            20                  25                  30

Cys Leu Leu Leu Ala Ala Gly Val Gly Ile Tyr Leu Leu Pro Asn
        35                  40                  45

Arg

<210> SEQ ID NO: 11
<211> LENGTH: 49
<212> TYPE: PRT
<213> ORGANISM: Viral

<400> SEQUENCE: 11

Gly Arg Leu Asp Leu Ser Gly Trp Phe Thr Ala Gly Tyr Ser Gly Gly
1               5                   10                  15

Asp Ile Tyr His Ser Val Ser His Ala Arg Pro Arg Trp Phe Trp Phe
            20                  25                  30

Cys Leu Leu Leu Ala Ala Gly Val Gly Ile Tyr Leu Leu Pro Asn
        35                  40                  45

Arg

<210> SEQ ID NO: 12
<211> LENGTH: 49
<212> TYPE: PRT
<213> ORGANISM: Viral

<400> SEQUENCE: 12

Ser Gln Leu Asp Leu Ser Ser Trp Phe Val Ala Gly Tyr Ser Gly Gly
1               5                   10                  15

Asp Ile Tyr His Ser Leu Ser Arg Ala Arg Pro Arg Trp Phe Met Trp
            20                  25                  30

Cys Leu Leu Leu Ser Val Gly Val Gly Ile Tyr Leu Leu Pro Asn
        35                  40                  45

Arg

<210> SEQ ID NO: 13
<211> LENGTH: 49
<212> TYPE: PRT
<213> ORGANISM: Viral

<400> SEQUENCE: 13

-continued

Ser Gln Leu Asp Leu Ser Ser Trp Phe Val Ala Gly Tyr Ser Gly Gly
1               5                   10                  15

Asp Ile Tyr His Ser Leu Ser Arg Ala Arg Pro Arg Trp Phe Met Trp
                20                  25                  30

Cys Leu Leu Leu Ser Val Gly Val Gly Ile Tyr Leu Leu Pro Asn
            35                  40                  45

Arg

<210> SEQ ID NO: 14
<211> LENGTH: 49
<212> TYPE: PRT
<213> ORGANISM: Viral

<400> SEQUENCE: 14

Ser Gln Leu Asp Leu Ser Asn Trp Phe Val Ala Gly Tyr Ser Gly Gly
1               5                   10                  15

Asp Val Tyr His Ser Leu Ser Arg Ala Arg Pro Arg Trp Phe Met Leu
                20                  25                  30

Cys Leu Leu Leu Ser Val Gly Val Gly Ile Tyr Leu Leu Pro Asn
            35                  40                  45

Arg

<210> SEQ ID NO: 15
<211> LENGTH: 49
<212> TYPE: PRT
<213> ORGANISM: Viral

<400> SEQUENCE: 15

Ser Gln Leu Asp Leu Ser Asn Trp Phe Val Ala Gly Tyr Ser Gly Gly
1               5                   10                  15

Asp Val Tyr His Ser Leu Ser Arg Ala Arg Pro Arg Trp Phe Met Leu
                20                  25                  30

Cys Leu Leu Leu Ser Val Gly Val Gly Ile Tyr Leu Leu Pro Asn
            35                  40                  45

Arg

<210> SEQ ID NO: 16
<211> LENGTH: 49
<212> TYPE: PRT
<213> ORGANISM: Viral

<400> SEQUENCE: 16

Ser Gln Leu Asp Leu Ser Lys Trp Phe Val Ala Gly Tyr Gly Gly Gly
1               5                   10                  15

Asp Ile Tyr His Ser Leu Ser Arg Ala Arg Pro Arg Trp Phe Met Leu
                20                  25                  30

Cys Leu Leu Leu Ser Val Gly Val Gly Ile Tyr Leu Leu Pro Asn
            35                  40                  45

Arg

<210> SEQ ID NO: 17
<211> LENGTH: 49
<212> TYPE: PRT
<213> ORGANISM: Viral

<400> SEQUENCE: 17

Ser Arg Leu Asp Leu Ser Gly Trp Phe Val Ala Gly Tyr Ser Gly Gly
1               5                   10                  15

```
Asp Ile Tyr His Ser Leu Ser Arg Ala Arg Pro Arg Trp Phe Met Leu
             20                  25                  30

Cys Leu Leu Leu Ser Val Gly Val Gly Ile Tyr Leu Leu Pro Asn
         35                  40                  45

Arg

<210> SEQ ID NO: 18
<211> LENGTH: 49
<212> TYPE: PRT
<213> ORGANISM: Viral

<400> SEQUENCE: 18

Ser Arg Leu Asp Leu Ser Gly Trp Phe Val Ala Gly Tyr Ser Gly Gly
1               5                   10                  15

Asp Ile Tyr His Ser Leu Ser Arg Ala Arg Pro Arg Trp Phe Met Leu
             20                  25                  30

Cys Leu Leu Leu Ser Val Gly Val Gly Ile Tyr Leu Leu Pro Asn
         35                  40                  45

Arg

<210> SEQ ID NO: 19
<211> LENGTH: 49
<212> TYPE: PRT
<213> ORGANISM: Viral

<400> SEQUENCE: 19

Ser Gln Leu Asp Leu Ser Gly Trp Phe Val Ala Gly Tyr Ser Gly Gly
1               5                   10                  15

Asp Ile Tyr His Ser Leu Ser Arg Ala Arg Pro Arg Trp Phe Leu Leu
             20                  25                  30

Cys Leu Leu Leu Ser Val Gly Val Gly Ile Tyr Leu Leu Pro Asn
         35                  40                  45

Arg

<210> SEQ ID NO: 20
<211> LENGTH: 49
<212> TYPE: PRT
<213> ORGANISM: Viral

<400> SEQUENCE: 20

Ser Gln Leu Asp Leu Ser Gly Trp Phe Val Ala Gly Tyr Ser Gly Gly
1               5                   10                  15

Asp Ile Tyr His Ser Leu Ser Arg Ala Arg Pro Arg Trp Phe Pro Leu
             20                  25                  30

Cys Leu Leu Leu Phe Val Gly Val Gly Ile Tyr Leu Leu Pro Asn
         35                  40                  45

Arg

<210> SEQ ID NO: 21
<211> LENGTH: 49
<212> TYPE: PRT
<213> ORGANISM: Viral

<400> SEQUENCE: 21

Ser Gln Leu Asp Leu Ser Gly Trp Phe Val Ala Gly Tyr Asn Gly Gly
1               5                   10                  15

Asp Ile Tyr His Ser Leu Ser Arg Ala Arg Pro Arg Trp Phe Met Leu
             20                  25                  30
```

-continued

Cys Leu Leu Leu Leu Ser Val Gly Val Gly Ile Tyr Leu Leu Pro Asn
                35                  40                  45
Arg

<210> SEQ ID NO: 22
<211> LENGTH: 49
<212> TYPE: PRT
<213> ORGANISM: Viral

<400> SEQUENCE: 22

Ser Arg Leu Asp Leu Ser Gly Trp Phe Val Ala Gly Tyr Gly Gly
1               5                   10                  15

Asp Ile Tyr His Ser Leu Ser Arg Ala Arg Pro Arg Trp Phe Met Leu
                20                  25                  30

Cys Leu Leu Leu Ser Val Gly Val Gly Ile Tyr Leu Leu Pro Asn
                35                  40                  45
Arg

<210> SEQ ID NO: 23
<211> LENGTH: 49
<212> TYPE: PRT
<213> ORGANISM: Viral

<400> SEQUENCE: 23

Ser Gln Leu Asp Leu Ser Gly Trp Phe Val Ala Gly Tyr Ser Gly Gly
1               5                   10                  15

Asp Ile Tyr His Ser Val Ser Arg Ala Arg Pro Arg Trp Phe Met Trp
                20                  25                  30

Cys Leu Leu Leu Ser Val Gly Val Gly Ile Tyr Leu Leu Pro Asn
                35                  40                  45
Arg

<210> SEQ ID NO: 24
<211> LENGTH: 49
<212> TYPE: PRT
<213> ORGANISM: Viral

<400> SEQUENCE: 24

Ser Gln Leu Asp Leu Ser Gly Trp Phe Val Ala Gly Tyr Ser Gly Gly
1               5                   10                  15

Asp Ile Tyr His Ser Val Ser Arg Ala Arg Pro Arg Trp Phe Met Trp
                20                  25                  30

Cys Leu Leu Leu Ser Val Gly Val Gly Ile Tyr Leu Leu Pro Asn
                35                  40                  45
Arg

<210> SEQ ID NO: 25
<211> LENGTH: 49
<212> TYPE: PRT
<213> ORGANISM: Viral

<400> SEQUENCE: 25

Ser Gln Leu Asp Leu Ser Ser Trp Phe Val Ala Gly Tyr Ser Gly Gly
1               5                   10                  15

Asp Ile Tyr His Ser Leu Ser Arg Ala Arg Pro Arg Trp Phe Met Trp
                20                  25                  30

Cys Leu Leu Leu Ser Val Gly Val Gly Ile Tyr Leu Leu Pro Asn
                35                  40                  45

Arg

```
<210> SEQ ID NO: 26
<211> LENGTH: 49
<212> TYPE: PRT
<213> ORGANISM: Viral

<400> SEQUENCE: 26
```

Ser Gln Leu Asp Leu Ser Gly Trp Phe Val Ala Gly Tyr Ser Gly Gly
1               5                   10                  15

Asp Ile Tyr His Ser Leu Ser Arg Ala Arg Pro Arg Trp Phe Met Trp
            20                  25                  30

Cys Leu Leu Leu Leu Ser Val Gly Val Gly Ile Tyr Leu Leu Pro Asn
        35                  40                  45

Arg

```
<210> SEQ ID NO: 27
<211> LENGTH: 49
<212> TYPE: PRT
<213> ORGANISM: Viral

<400> SEQUENCE: 27
```

Ser Gln Leu Asp Leu Ser Gly Trp Phe Val Ala Gly Tyr Ser Gly Gly
1               5                   10                  15

Asp Ile Tyr His Ser Leu Ser Arg Ala Arg Pro Arg Trp Phe Met Trp
            20                  25                  30

Cys Leu Leu Leu Leu Ser Val Gly Val Gly Ile Tyr Leu Leu Pro Asn
        35                  40                  45

Arg

```
<210> SEQ ID NO: 28
<211> LENGTH: 49
<212> TYPE: PRT
<213> ORGANISM: Viral

<400> SEQUENCE: 28
```

Ser Arg Leu Asp Leu Ser Gly Trp Phe Val Ala Gly Tyr Ser Gly Gly
1               5                   10                  15

Asp Ile Tyr His Ser Leu Ser Arg Ala Arg Pro Arg Trp Phe Met Leu
            20                  25                  30

Cys Leu Leu Leu Leu Ser Val Gly Val Gly Ile Tyr Leu Leu Pro Asn
        35                  40                  45

Arg

```
<210> SEQ ID NO: 29
<211> LENGTH: 49
<212> TYPE: PRT
<213> ORGANISM: Viral

<400> SEQUENCE: 29
```

Ser Arg Leu Asp Leu Ser Ser Trp Phe Val Ala Gly Tyr Ser Gly Gly
1               5                   10                  15

Asp Ile Tyr His Ser Val Ser His Ala Arg Pro Arg Trp Phe Met Leu
            20                  25                  30

Cys Leu Leu Leu Leu Ser Val Gly Val Gly Ile Tyr Leu Leu Pro Asn
        35                  40                  45

Arg

<210> SEQ ID NO: 30
<211> LENGTH: 49
<212> TYPE: PRT
<213> ORGANISM: Viral

<400> SEQUENCE: 30

Ser Gln Leu Asp Leu Ser Gly Trp Phe Val Ala Gly Tyr Ser Gly Gly
1               5                   10                  15

Asp Ile Tyr His Ser Leu Ser Arg Ala Arg Pro Arg Trp Phe Met Leu
            20                  25                  30

Cys Leu Leu Leu Ser Val Gly Val Gly Ile Tyr Leu Leu Pro Asn
        35                  40                  45

Arg

<210> SEQ ID NO: 31
<211> LENGTH: 49
<212> TYPE: PRT
<213> ORGANISM: Viral

<400> SEQUENCE: 31

Gly Gln Leu Asp Leu Ser Ser Trp Phe Thr Val Gly Val Gly Gly Asn
1               5                   10                  15

Asp Ile Tyr His Ser Val Ser Arg Ala Arg Thr Arg Tyr Leu Leu Leu
            20                  25                  30

Cys Leu Leu Leu Thr Val Gly Val Gly Ile Phe Leu Leu Pro Ala
        35                  40                  45

Arg

<210> SEQ ID NO: 32
<211> LENGTH: 49
<212> TYPE: PRT
<213> ORGANISM: Viral

<400> SEQUENCE: 32

Gly Gln Leu Asp Leu Ser Ser Trp Phe Thr Val Gly Val Gly Gly Asn
1               5                   10                  15

Asp Ile Tyr His Ser Val Ser Arg Ala Arg Thr Arg His Leu Leu Leu
            20                  25                  30

Cys Leu Leu Leu Thr Val Gly Val Gly Ile Phe Leu Leu Pro Ala
        35                  40                  45

Arg

<210> SEQ ID NO: 33
<211> LENGTH: 51
<212> TYPE: PRT
<213> ORGANISM: Viral

<400> SEQUENCE: 33

Leu Gln Gly Lys His Tyr Glu Gln Leu Gln Leu Arg Thr Glu Thr Asn
1               5                   10                  15

Pro Val Met Gly Val Gly Thr Glu Arg Tyr Lys Leu Gly Pro Ile Val
            20                  25                  30

Asn Leu Leu Leu Arg Arg Leu Lys Ile Leu Leu Met Thr Ala Val Gly
        35                  40                  45

Val Ser Ser
    50

<210> SEQ ID NO: 34
<211> LENGTH: 48

```
<212> TYPE: PRT
<213> ORGANISM: Viral

<400> SEQUENCE: 34

Gly Arg His Tyr Glu Glu Leu Val Leu Ala Arg Lys Gln Phe Asn Asn
1               5                   10                  15

Phe Gln Gly Thr Asp Arg Tyr Asn Leu Gly Pro Ile Val Asn Met Val
            20                  25                  30

Leu Arg Arg Leu Arg Val Met Met Met Thr Leu Ile Gly Arg Gly Val
        35                  40                  45
```